(12) United States Patent
Sellars et al.

(10) Patent No.: US 10,842,096 B1
(45) Date of Patent: Nov. 24, 2020

(54) FLUE GAS RECLAMATION SYSTEM AND METHOD

(71) Applicant: HONDA MOTOR CO., LTD., Tokyo (JP)

(72) Inventors: Daniel T. Sellars, West Liberty, OH (US); Joel W. Agner, Bluffton, OH (US)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 16/593,159

(22) Filed: Oct. 4, 2019

(51) Int. Cl.
  *A01G 33/00* (2006.01)
  *A01G 9/18* (2006.01)
  *F01K 27/00* (2006.01)

(52) U.S. Cl.
  CPC ............ *A01G 33/00* (2013.01); *A01G 9/18* (2013.01); *F01K 27/00* (2013.01); *Y02E 50/12* (2013.01)

(58) Field of Classification Search
  CPC .......... F01K 27/00; F01K 27/02; F01K 23/00; F01K 23/06; F01K 23/065; F01K 17/025; C12M 23/18; C12M 23/44; C12M 31/06; A01G 33/00; A01G 9/18; Y02E 50/12
  USPC ............ 60/616, 641.2, 645, 698; 47/1.4, 60; 435/257.1, 262.5
  See application file for complete search history.

(56) References Cited

U.S. PATENT DOCUMENTS

| | | | |
|---|---|---|---|
| 7,191,736 B2 * | 3/2007 | Goldman | ............... F02B 43/02 60/776 |
| 8,361,786 B2 | 1/2013 | Hu et al. | |
| 8,685,707 B2 | 4/2014 | Plechinger | |
| 9,222,480 B2 | 12/2015 | Younes et al. | |
| 9,961,840 B2 | 5/2018 | Chen et al. | |
| 2008/0155985 A1* | 7/2008 | Labrador | ............... F01K 27/00 60/698 |
| 2008/0220486 A1 | 9/2008 | Weiss | |
| 2014/0199759 A1 | 7/2014 | Van Alstyne et al. | |
| 2017/0107478 A1 | 4/2017 | Harmon et al. | |
| 2017/0341942 A1 | 11/2017 | Harper, Jr. | |

FOREIGN PATENT DOCUMENTS

| | | |
|---|---|---|
| CN | 202014482 A | 10/2011 |
| CN | 105046371 A | 11/2015 |
| CN | 108266964 A | 7/2018 |

* cited by examiner

*Primary Examiner* — Thai Ba Trieu
*Assistant Examiner* — Dapinder Singh
(74) *Attorney, Agent, or Firm* — Plumsea Law Group, LLC (57) ABSTRACT

A method and system for flue gas reclamation is described. In one embodiment, a flue gas reclamation system is provided. The system includes a combustion engine including an intake member, an output shaft, and an exhaust outlet. The intake member receives flue gas from a gas source. A generator is connected to the output shaft and a compressor is connected to the exhaust outlet of the combustion engine. At least one holding tank is connected to the compressor and the compressor stores enriched flue gas from the exhaust outlet of the combustion engine in the at least one holding tank. A battery is connected to the generator and is configured to provide electric power to the flue gas reclamation system. An algae farm in fluid communication with the at least one holding tank is configured to receive the stored enriched flue gas from the at least one holding tank.

20 Claims, 5 Drawing Sheets

FLUE GAS RECLAMATION SYSTEM AND METHOD

BACKGROUND

The present disclosure relates to the field of environmental protection, and, more particularly, to a flue gas reclamation system and method.

Flue gas is an exhaust gas produced as a result of combustion of fossil fuels by industrial facilities, such as power plants, iron or steel foundries, or other sources. Flue gas contains the reaction products from combustion, as well as various residual components, including particulate matter, sulfur oxides, nitrogen oxides, carbon dioxide, and carbon monoxide, as well as other substances that may vary based on the fuel type, fuel composition, and the combustion conditions, such as the air-fuel ratio. Many of these flue gas components are air pollutants and are required by governmental regulations to be eliminated or minimized by the flue gas producing facilities using special cleaning or mediation procedures before the flue gas may be released into the atmosphere.

Conventional techniques for limiting the values of pollutants in flue gas to comply with governmental regulations include various flue gas cleaning systems or treatments, such as electrostatic precipitators, gas scrubbers, or dust filters, that attempt to reduce the amount of emitted pollutants. Some of these conventional approaches can effectively remove 90 percent or more of certain pollutants, however, they can be costly to install and operate. Additionally, effective flue gas treatments can vary widely from one facility to another, and various governmental regulations may impose stricter limits than others.

SUMMARY

In one aspect, a flue gas reclamation system is provided, the system comprising: a combustion engine including an intake member, an output shaft, and an exhaust outlet, the intake member of the combustion engine configured to receive flue gas from a gas source; a generator connected to the output shaft of the combustion engine; a compressor connected to the exhaust outlet of the combustion engine; at least one holding tank connected to the compressor, wherein the compressor stores enriched flue gas from the exhaust outlet of the combustion engine in the at least one holding tank; a battery connected to the generator, the battery configured to provide electric power to the flue gas reclamation system; and an algae farm in fluid communication with the at least one holding tank, wherein the algae farm is configured to receive the stored enriched flue gas from the at least one holding tank.

In another aspect, a portable flue gas reclamation system is provided, the system comprising: a portable transport apparatus including at least one set of wheels configured for moving the portable transport apparatus; a combustion engine disposed inside the portable transport apparatus, the combustion engine including an intake member, an output shaft, and an exhaust outlet, the intake member of the combustion engine configured to receive flue gas from a gas source; a generator disposed inside the portable transport apparatus, the generator connected to the output shaft of the combustion engine; a compressor disposed inside the portable transport apparatus, the compressor connected to the exhaust outlet of the combustion engine; and at least one holding tank disposed inside the portable transport apparatus, the at least one holding tank connected to the compressor, wherein the compressor stores enriched flue gas from the exhaust outlet of the combustion engine in the at least one holding tank; and wherein the stored enriched flue gas from the at least one holding tank is configured to be supplied to an algae farm in fluid communication with the at least one holding tank.

In still another aspect, a method for reclaiming flue gas from a gas source for use in an algae farm is provided, the method comprising: receiving flue gas from a gas source; supplying the received flue gas to an intake member of a combustion engine; providing enriched flue gas from an exhaust outlet of the combustion engine to a compressor; compressing the enriched flue gas for storage in at least one holding tank; and supplying the enriched flue gas from the least one holding tank to an algae farm.

Other systems, methods, features and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DETAILED DESCRIPTION

A flue gas reclamation system and associated method are described herein. According to the techniques of the example embodiments, the described flue gas reclamation system may be used to provide energy and nutrients to a biotic cultivation, harvesting, and processing system, such as an algae farm.

Figure 1:
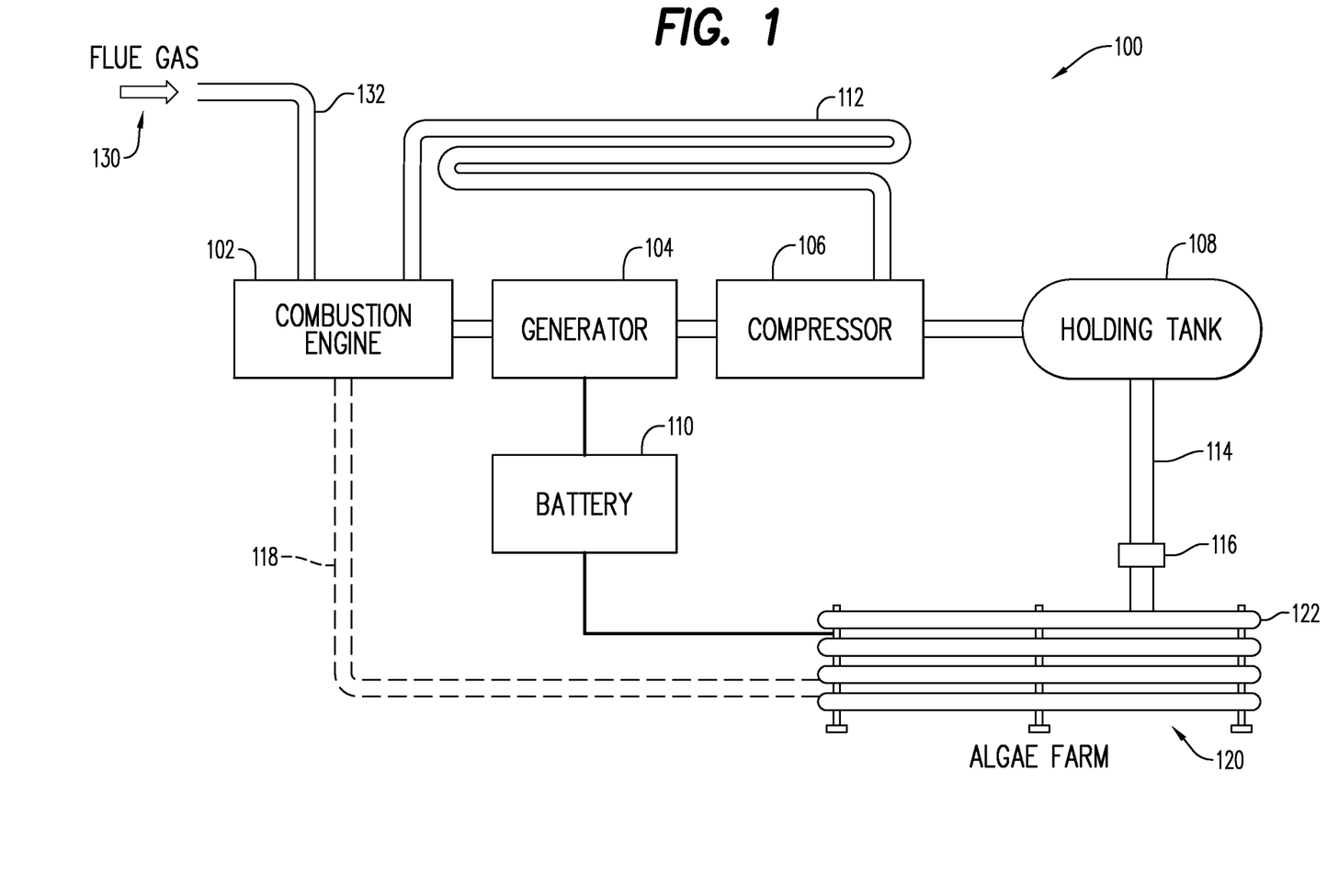
FIG. 1 is a schematic view of an example embodiment of a flue gas reclamation system.

Referring now to FIG. 1, a schematic view of an example embodiment of a flue gas reclamation system 100 is shown. In an example embodiment, flue gas reclamation system 100 may be associated with any source of flue gas, for example, industrial facilities, such as power plants, iron or steel foundries, or other sources. Flue gas reclamation system 100 is configured to use the flue gas from such gas sources to assist with remediation of the gas, as well as to provide electrical generation, heat, and/or nutrients to an algae farm, for example, algae farm 120.

In this embodiment, flue gas reclamation system 100 includes a combustion engine 102, a generator 104, a compressor 106, at least one holding tank 108, and a battery 110. In an example embodiment, combustion engine 102 may be any type of internal combustion engine (ICE) that is configured to combust fuel. In one embodiment, combustion engine 102 is a diesel engine. However, it should be understood that combustion engine 102 may be any type of engine that is capable of combustion of fuel to produce energy.

In this embodiment, combustion engine 102 includes at least an intake member, an output shaft, and an exhaust outlet, as well as additional components that are conventionally included in a combustion engine. In this embodiment, the intake member of combustion engine 102 is configured to receive the flue gas from the gas source. Upon receiving the flue gas, combustion engine 102 mixes the received flue gas with fuel for combustion. In some embodiments, additional air may be introduced into the intake member of combustion engine 102, as needed, to attain an appropriate air-fuel ratio for the combustion. In various embodiments, any type of fuel may be provided to combustion engine 102, including, but not limited to: diesel, gasoline, kerosene, propane, natural gas, or other types of fuel. In one embodiment, combustion engine 102 is a diesel engine configured to use waste vegetable oil for fuel. In such embodiments, the waste vegetable oil may be obtained and/or processed by the same facility that generates the flue gas or may be provided from other sources.

In an example embodiment, generator 104 is configured to convert mechanical energy obtained from an external source, for example, combustion engine 102, into electrical energy. For example, in this embodiment, generator 104 is connected to the output shaft of combustion engine 102 and converts the mechanical energy produced by combustion engine 102 into electricity. In an example embodiment, the electricity produced by generator 104 may be used by flue gas reclamation system 100 to provide power to the various components. For example, electricity from generator 104 can be used to charge battery 110 and provide power to compressor 106, as well as to pumps, meters, control systems, or other electrical equipment associated with flue gas reclamation system 100. In addition, in other embodiments, generator 104 may be used to generate electricity for use external to flue gas reclamation system 100.

In this embodiment, battery 110 is shown as a separate component for storing the electrical energy produced by generator 104. In other embodiments, battery 110 may be a part of, or associated with, another component or device. For example, in one embodiment, battery 110 is provided in an electric vehicle. With this arrangement, the electrical energy produced by generator 104 may further be used to assist with charging battery 110 for use by the electric vehicle. In addition, the electric vehicle may be configured with its own supplemental power source, such as an internal combustion engine or solar panels, that can also provide charging to battery 110 and/or ensure that power is available to flue gas reclamation system 100 on a consistent and continuous basis.

In this embodiment, compressor 106 is connected to the exhaust outlet of combustion engine 102 and is configured to compress enriched flue gas exiting the exhaust outlet of combustion engine 102 for storage. For example, compressor 106 may store the compressed enriched flue gas in the at least one holding tank 108 connected to compressor 106. In this embodiment, one holding tank 108 is shown, but it should be understood that any number of holding tanks may be provided as part of flue gas reclamation system 100.

Additionally, in some embodiments, compressor 106 may also be connected to the output shaft of combustion engine 102 to further drive compressor 106. Compressor 106 may be connected to the same output shaft as generator 104, for example, through a power takeoff (PTO) unit or accessory drive. In addition, in some embodiments, compressor 106 may be configured to run backwards (i.e., in the opposite direction) to recover compression energy from the enriched flue gas.

In some embodiments, the exhaust from combustion engine 102 (i.e., the enriched flue gas) may be configured to pass through a cooling heat exchanger 112 prior to being received by compressor 106. As shown in FIG. 1, cooling heat exchanger 112 includes a series of tubes or pipes that the hot exhaust from combustion engine 102 can pass through to cool down via heat exchange with the ambient air before arriving at compressor 106. With this arrangement, the hot exhaust gas from combustion engine 102 may be cooled before being compressed by compressor 106, thereby reducing the operating temperatures of the components and making compression of the enriched flue gas more efficient for compressor 106.

In an example embodiment, algae farm 120 is in fluid communication with the at least one holding tank 108. For example, as shown in FIG. 1, algae farm 120 is connected to holding tank 108 via a pipe 114. In this embodiment, a solenoid 116, for example, a sparging solenoid, is configured to control the flow of the stored enriched flue gas from holding tank 108 to algae farm 120 through pipe 114. With this configuration, by opening or closing solenoid 116, algae farm 120 can receive the stored enriched flue gas from holding tank 108 through pipe 114.

In this embodiment, algae farm 120 includes a plurality of tubes 122 that are configured to hold the algae and water or other growth media. In an example embodiment, plurality of tubes 122 may be glass or other transparent material that allows sunlight to pass through into the interior so that the algae contained within tubes may conduct photosynthesis. In the presence of sunlight, water, and the carbon dioxide from the enriched flue gas, the algae reproduce and grow. This process consumes the carbon dioxide contained in the enriched flue gas and traps it in the form of the algae biomass. In different embodiments, algae farm 120 may include many different species of algae. For example, most types of algae that are commercially grown in algae farms, such as algae farm 120, are microalgae. These microalgae may also be referred to as phytoplankto, microphytes, and/or planktonic algae. However, in other embodiments, any suitable type of algae may be used in algae farm 120.

In some embodiments, the algae biomass from algae farm 120 may be processed to generate fuel. For example, ion one embodiment, hydrothermal liquefaction (HTL) may be used to convert the algae biomass from algae farm 120 into a crude-like oil (also sometimes referred to as bio-oil or biocrude) upon application of moderate temperature and high pressure. Additionally, in some embodiments, waste heat from combustion engine 120 may be used as part of the hydrothermal liquefaction process of the algae in algae farm 120. With this arrangement, flue gas reclamation system 100 can use algae from algae farm 120 to produce fuel which may be used to operate combustion engine 102 or may be provided to external sources. In other embodiments, the processed biomass may also be converted for other uses, such as chemical, pharmaceutical, or feedstock.

In some embodiments, flue gas reclamation system 100 may include a coolant system 118 associated with combustion engine 102. For example, as shown in FIG. 1, coolant system 118 may be in fluid communication with combustion engine 102. In an example embodiment, coolant system 118 may be routed to various components of flue gas reclamation system 100, including at least one of an evaporative cooler or a heat exchanger in fluid communication with coolant system 118. For example, in hot weather, coolant system 118 may supply coolant from combustion engine 102 to the evaporative cooler to assist with heat dissipation. In cold weather, coolant system 118 may supply coolant from combustion engine 102 to the heat exchanger disposed in or in communication with the algae growth media of algae farm 120 to assist with regulating or controlling the temperature of the fluid in algae farm 120 and, thereby, promote efficient growth and reproduction of the algae. In other embodiments, the waste heat from combustion engine 102 may also be used for other purposes. For example, the waste heat may be used for processing and/or drying of the harvested algae biomass (e.g., from algae farm 120) and/or may be provided to external sources outside of flue gas reclamation system 100.

Additionally, in some embodiments, the combustion characteristics of combustion engine 102 may be optimized to promote growth of the algae in algae farm 120. For example, in one embodiment, the combustion characteristics of combustion engine 120 can be optimized to fix nitrogen from the intake air for use as fertilizer by the algae during photosynthesis. Other combustion characteristics may also be optimized for the specific growth benefits provided to the algae, such as altering the air-fuel ratio to reduce oxygen.

In an example embodiment, flue gas 130 from a gas source, such as an industrial facility discussed above, may be supplied to flue gas reclamation system 100 via a pipe 132. For example, pipe 132 may connect to an exhaust outlet or other component associated with the gas source which vents or releases flue gas 130. With this arrangement, pipe 132 routes flue gas 130 from the gas source into flue gas reclamation system 100 so that flue gas 130 may be processed and used by the algae in algae farm 120.

Figure 2:
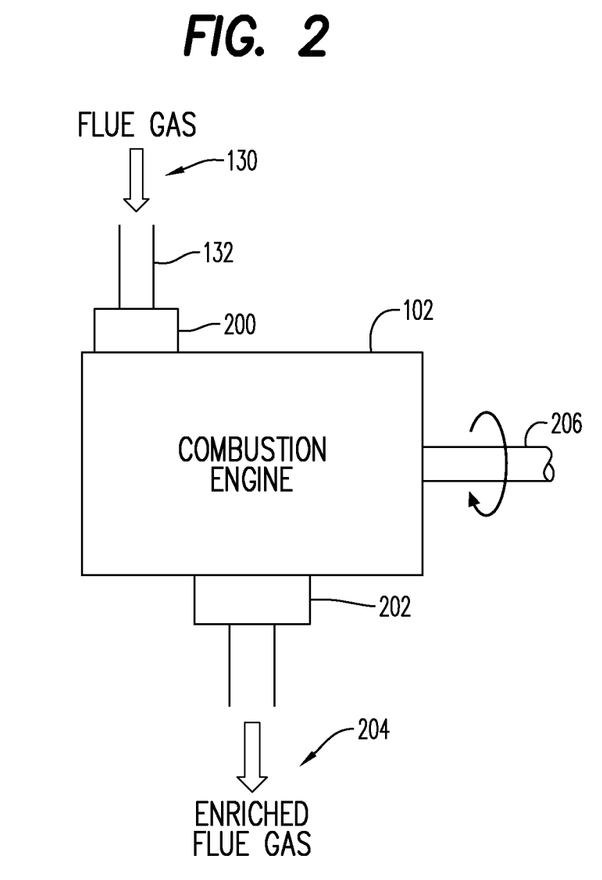
FIG. 2 is an enlarged view of an example embodiment of a combustion engine.

Referring now to FIG. 2, an enlarged view of the example embodiment of combustion engine 102 is shown. In this embodiment, combustion engine 102 includes an intake member 200 that is configured to receive flue gas 130 via pipe 132. As described above, combustion engine 102 uses flue gas 130 for combustion of fuel and the resulting by-product is enriched flue gas 204, which exits combustion engine 102 through an exhaust outlet 202. For example, as described above, enriched flue gas 204 may be received by compressor 106 connected to combustion engine 102 via exhaust outlet 202. The mechanical energy generated by combustion engine 102 may be used to turn an output shaft 206. As described above, in some embodiments, output shaft 206 may be connected to generator 104 and/or compressor 106 (e.g., via a PTO or accessory drive), as well as other components of flue gas reclamation system 100.

Figure 3:
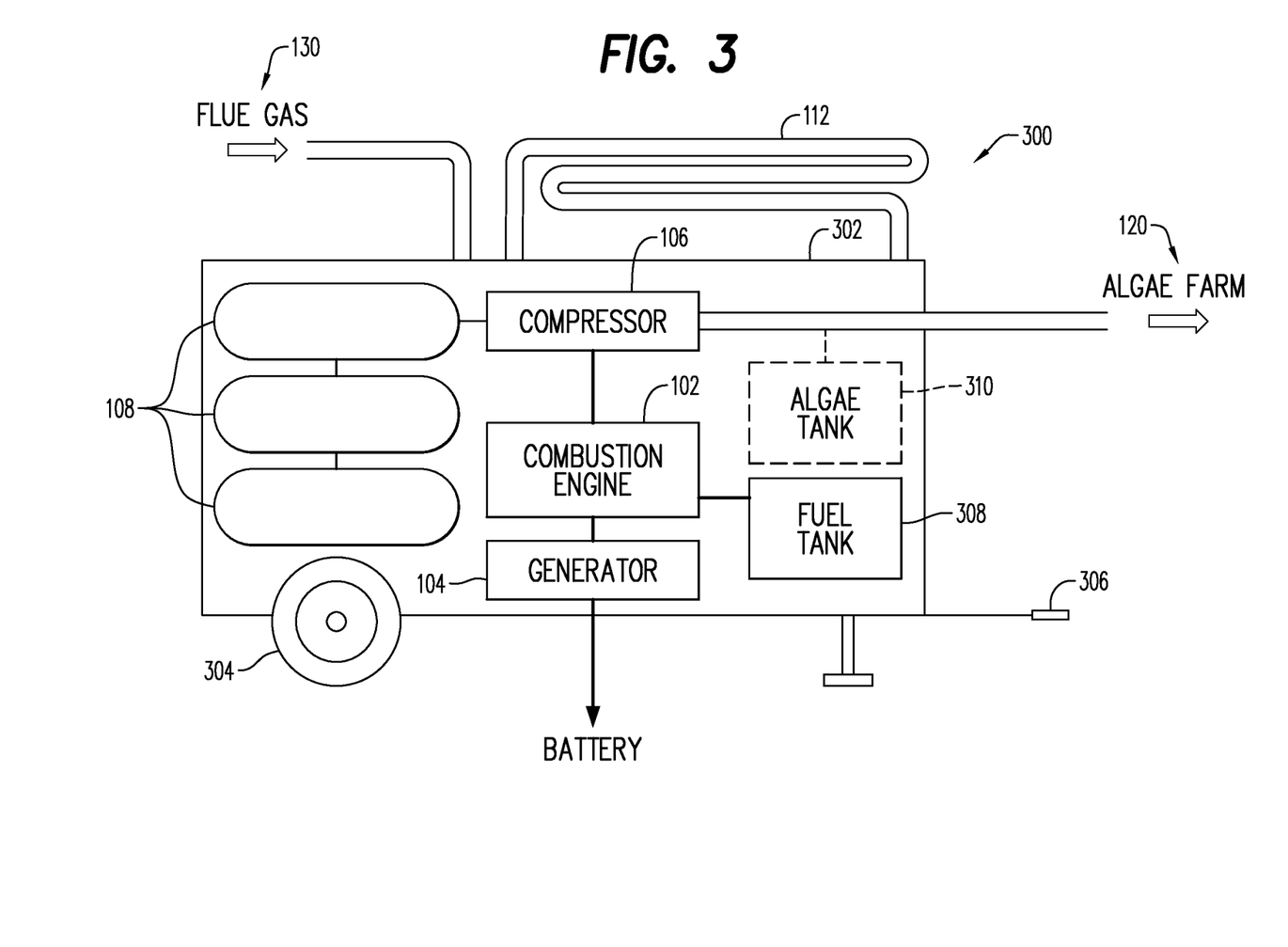
FIG. 3 is a schematic view of an example embodiment of a portable flue gas reclamation system.

FIG. 3 is a schematic view of an example embodiment of a portable flue gas reclamation system 300. In some embodiments, components of a flue gas reclamation system (e.g., flue gas reclamation system 100) may be configured to be portable so that the flue gas reclamation system may be moved from location to location. In an example embodiment, portable flue gas reclamation system 300 includes at least combustion engine 102, generator 104, compressor 106, and one or more holding tanks 108. In this embodiment, portable flue gas reclamation system 300 also includes cooling heat exchanger 112. It should be understood that in other embodiments, additional or alternate components may be provided as part of portable flue gas reclamation system 300.

In this embodiment, portable flue gas reclamation system 300 includes a portable transport apparatus 302. Portable transport apparatus 302 includes at least one set of wheels 304 that are configured for moving portable transport apparatus 302. In one embodiment, portable transport apparatus 302 is a trailer that includes combustion engine 102, generator 104, compressor 106, and one or more holding tanks 108 disposed inside portable transport apparatus 302. In addition, cooling heat exchanger 112, in the form of a plurality of tubes or pipes, is disposed on top of portable transport apparatus 302. With this arrangement, the hot exhaust gas may pass through the tubes of cooling heat exchanger 112 exposed on the outside of portable transport apparatus 302 and use the ambient air to cool the exhaust gas and reduce its temperature.

In this embodiment, portable transport apparatus 302 also includes a connection member 306, such as a hitch or receiver, that is configured to attach or engage with another vehicle to assist with moving portable transport apparatus 302 from one location to another. For example, portable transport apparatus 302 may be moved by a truck or other vehicle. In other embodiments, portable transport apparatus 302 may be a motor vehicle that is configured to move under its own power. In still other embodiments, portable transport apparatus 302 may be a shipping container or storage unit that is placed on-site and includes all of the components of portable flue gas reclamation system 300.

In this embodiment, electricity produced by generator 106, which is disposed inside portable transport apparatus 302 in this embodiment, can be supplied to a battery (e.g., battery 110, described above) for charging. In some embodiments, as described with reference to FIG. 1, the battery receiving electricity from generator 106 may be associated with or part of an electric vehicle. With this arrangement, electricity produced by generator 106 of portable flue gas reclamation system 300 using flue gas 130 may be used to power portable flue gas reclamation system 300, as well as provide additional charging capacity or power to a battery of an electric vehicle. In addition, as described above, the electric vehicle may also be used to provide supplemental or auxiliary power to portable flue gas reclamation system 300.

In this embodiment, portable transport apparatus 302 includes a fuel tank 308 that is configured to provide fuel to combustion engine 102 to use for combustion. In addition, in embodiments where portable transport apparatus 302 is a motor vehicle, fuel tank 308 may also be used to provide fuel to an engine that powers portable transport apparatus 302, which can be combustion engine 102 or a separate engine or motor.

As shown in this embodiment, portable flue gas reclamation system 300 is configured to receive flue gas 130 from a gas source in a similar manner as described above in reference to flue gas reclamation system 100. Similarly, portable flue gas reclamation system 300 is also configured to provide the enriched flue gas from combustion engine 102 that has been compressed by compressor 106 into holding tanks 108. From holding tanks 108, the enriched flue gas may then be provided to algae farm 120, as described above. In some embodiments, algae farm 120 may be located on-site, for example, near the gas source of flue gas 130, such as a building or industrial facility. In other embodiments, algae farm 120 may be self-contained within a portable unit, such as a shipping container or other apparatus that can be moved from one location to another along with portable flue gas reclamation system 300.

Additionally, in some embodiments, portable flue gas reclamation system 300 may include an optional algae tank 310 that is disposed inside portable transport apparatus 302. In these embodiments, algae tank 310 may hold a smaller volume of algae than algae farm 120 and may be used for smaller gas sources or facilities. In such cases, portable flue gas reclamation system 300 may further include additional components to permit harvesting and/or processing of the algae from algae tank 310, such as a centrifuge, harvesters, dryers, etc., so that the algae may be processed into useable biomass or biofuel directly by portable flue gas reclamation system 300.

Figure 4:
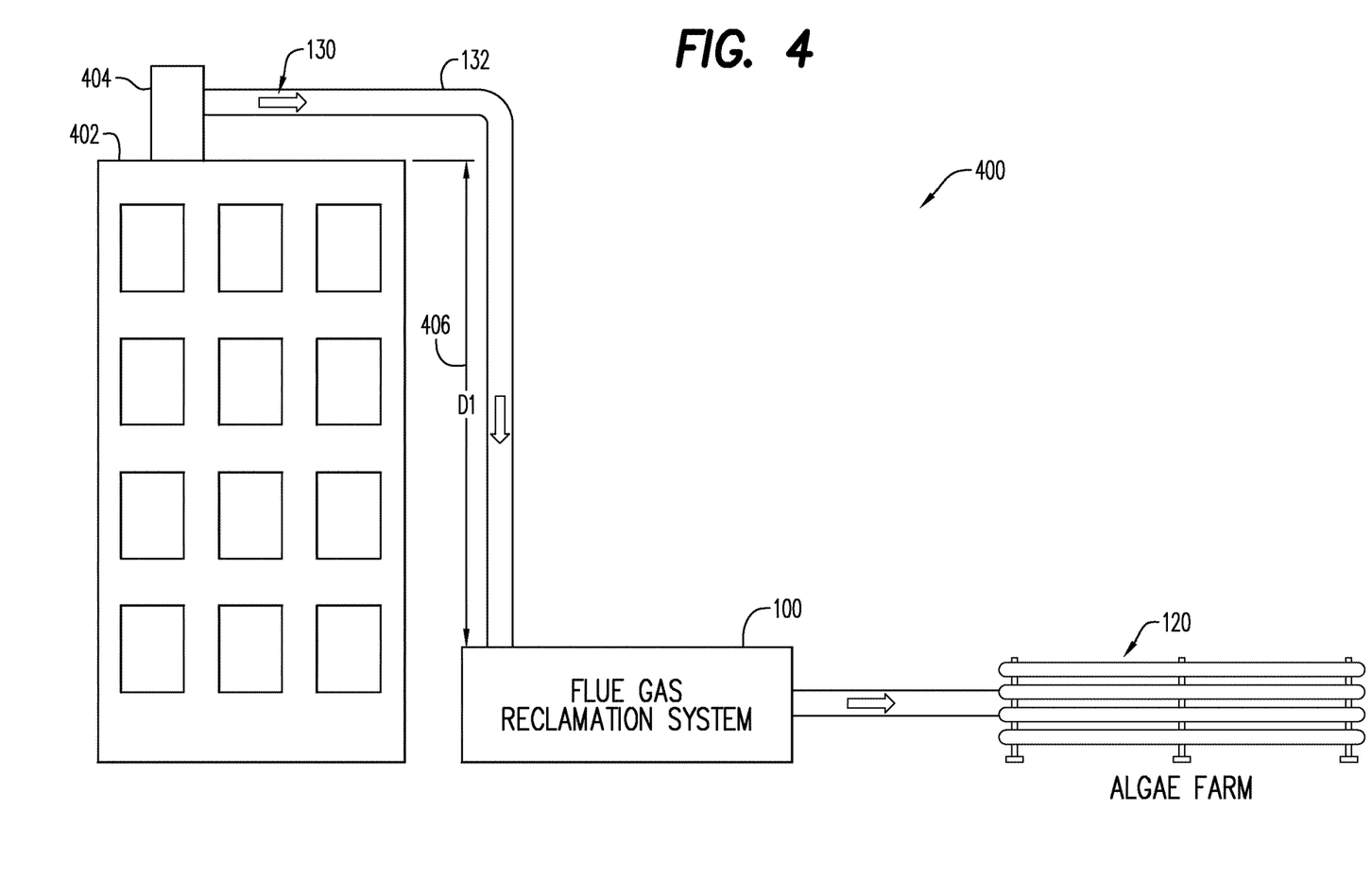
FIG. 4 is a representational view of an example embodiment of a flue gas reclamation system deployed at a building.

FIG. 4 is a representational view of an example embodiment of a flue gas reclamation system deployed at a location 400 near or adjacent to a building 402 that is a gas source of flue gas 130. In this embodiment, the flue gas reclamation system shown in FIG. 4 deployed at location 400 of building 402 is flue gas reclamation system 100, described above. In other embodiments, the flue gas reclamation system deployed at site 400 of building 402 may be portable flue gas reclamation system 300, described above. With this arrangement, an industrial facility (e.g., building 402) that generates flue gas may choose to install flue gas reclamation system 100 on-site or may choose to bring in one or more of portable flue gas reclamation system 300 to provide flue gas reclamation and processing of the flue gas generated by the facility. A facility may also be able to expand its capacity to handle additional or excess flue gas by adding additional portable flue gas reclamation systems 300 as needed to supplement an existing installation of a flue gas reclamation system (e.g., flue gas reclamation system 100 and/or portable flue gas reclamation system 300).

In this embodiment, building 402 includes an exhaust outlet 404 located on a roof of building 402 to vent or release flue gas 130 produced by building 402. As shown in FIG. 4, flue gas 130 from exhaust outlet 404 is routed to flue gas reclamation system 100 via pipe 132. In this embodiment, flue gas 130 is routed a first distance D1 406 from the roof of building 402 down to flue gas reclamation system 100. With this arrangement, flue gas reclamation system 100 may assist with pulling or drawing flue gas 130 from a higher location (i.e., roof of building 402) to a lower location (i.e., flue gas reclamation system 100) at or near the ground level of location 400. Additionally, as shown in this embodiment, flue gas 130 from building 402 is provided to algae farm 120 from flue gas reclamation system 100.

Figure 5:
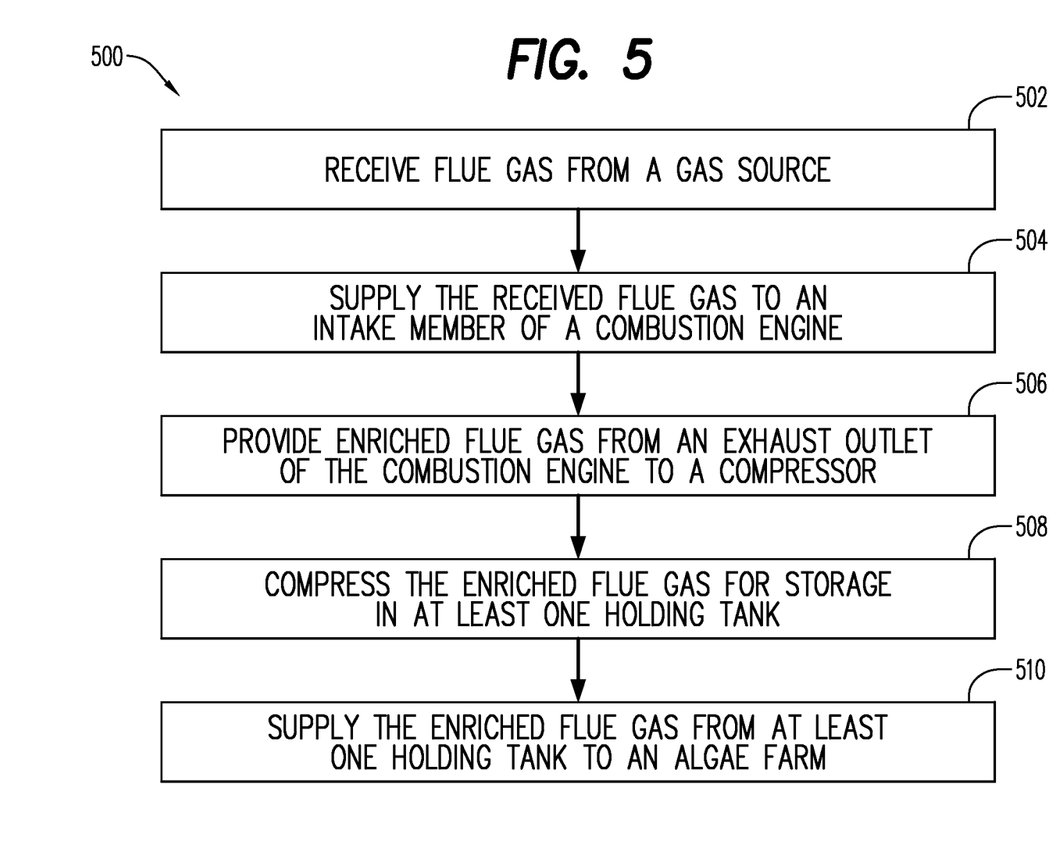
FIG. 5 is a flowchart of an example embodiment of a method for flue gas reclamation.

FIG. 5 is a flowchart of an example embodiment of a method 500 for flue gas reclamation. In an example embodiment, method 500 may be implemented using any of the embodiments of a flue gas reclamation system, including flue gas reclamation system 100 and/or portable flue gas reclamation system 300, described above.

In this embodiment, method 500 may begin at an operation 502, where flue gas is received from a source. For example, at operation 502 flue gas reclamation system 100 or portable flue gas reclamation system 300 receives flue gas 130 from a gas source, such as building 402 or another industrial facility. Next, method 500 includes an operation 504. At operation 504, the received flue gas is supplied to an intake member of a combustion engine. For example, flue gas 130 may be supplied to intake member 200 of combustion engine 102, as shown in FIG. 2.

Once the received flue gas is supplied to the combustion engine at operation 504, method 500 may further include an operation 506. At operation 506, the enriched flue gas from an exhaust outlet of the combustion engine (i.e., the combustion engine that received the flue gas at operation 504) is provided to a compressor. For example, as shown in FIG. 2, enriched flue gas 204 from exhaust outlet 202 of combustion engine 102 is provided to compressor 106. It should be understood that between operation 504 and operation 506, combustion engine 102 undergoes combustion. That is, the combustion engine uses the received flue gas from operation 504 and mixes it with fuel to cause a combustion process to occur. The byproducts of the combustion process make up the enriched flue gas that is provided to the compressor at operation 506.

Next, method 500 includes an operation 508 where the enriched flue gas received from operation 506 is compressed for storage in at least one holding tank. For example, as shown in FIG. 1 above, compressor 106 can receive flue gas enriched by combustion engine 102 and store it in one or more holding tanks 108. In this embodiment, method 500 further includes an operation 510. At operation 510, the stored enriched flue gas in the one or more holding tanks are supplied to an algae farm. For example, the enriched flue gas stored in holding tanks 108 can be supplied to algae farm 120 via pipe 114 by operation of solenoid 116 (i.e., by opening or closing solenoid 116 so that the flue gas flows from holding tanks 108 to algae farm 120).

With this arrangement, pollutants and carbon dioxide in flue gas from a gas source may be reduced or removed and the described flue gas reclamation system may be used to provide energy and nutrients to a biotic cultivation, harvesting, and processing system, such as algae farm 120.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

The invention claimed is:

1. A flue gas reclamation system, the system comprising:
   a combustion engine including an intake member, an output shaft, and an exhaust outlet, the intake member of the combustion engine configured to receive flue gas from a gas source;
   a generator connected to the output shaft of the combustion engine;
   a compressor connected to the exhaust outlet of the combustion engine;
   at least one holding tank connected to the compressor, wherein the compressor stores enriched flue gas from the exhaust outlet of the combustion engine in the at least one holding tank;
   a battery connected to the generator, the battery configured to provide electric power to the flue gas reclamation system; and
   an algae farm in fluid communication with the at least one holding tank, wherein the algae farm is configured to receive the stored enriched flue gas from the at least one holding tank.

2. The flue gas reclamation system according to claim 1, wherein the combustion engine, the generator, the compressor, and the at least one holding tank are provided together in a portable transport apparatus.

3. The flue gas reclamation system according to claim 1, wherein the battery is provided in an electric vehicle.

4. The flue gas reclamation system according to claim 1, further comprising:
   a cooling heat exchanger connected to the exhaust outlet and the compressor.

5. The flue gas reclamation system according to claim 1, further comprising:
   a coolant system associated with the combustion engine; and at least one of an evaporative cooler or a heat exchanger in fluid communication with the coolant system.

6. The flue gas reclamation system according to claim 5, wherein the heat exchanger is in fluid communication with an algae growth medium associated with the algae farm.

7. The flue gas reclamation system according to claim 1, wherein waste heat from the combustion engine is used for hydrothermal liquefaction of algae in the algae farm.

8. The flue gas reclamation system according to claim 1, further comprising a solenoid disposed in fluid communication between the at least one holding tank and the algae farm; and
wherein the solenoid is configured to control release of the stored enriched flue gas to the algae farm.

9. A portable flue gas reclamation system, the system comprising:
a portable transport apparatus configured to receive components of the portable flue gas reclamation system;
a combustion engine disposed inside the portable transport apparatus, the combustion engine including an intake member, an output shaft, and an exhaust outlet, the intake member of the combustion engine configured to receive flue gas from a gas source;
a generator disposed inside the portable transport apparatus, the generator connected to the output shaft of the combustion engine;
a compressor disposed inside the portable transport apparatus, the compressor connected to the exhaust outlet of the combustion engine; and
at least one holding tank disposed inside the portable transport apparatus, the at least one holding tank connected to the compressor, wherein the compressor stores enriched flue gas from the exhaust outlet of the combustion engine in the at least one holding tank; and
wherein the stored enriched flue gas from the at least one holding tank is configured to be supplied to an algae farm in fluid communication with the at least one holding tank.

10. The portable flue gas reclamation system according to claim 9, wherein the gas source is a building.

11. The portable flue gas reclamation system according to claim 10, wherein the flue gas is routed a first distance from a roof of the building down to the portable transport apparatus.

12. The portable flue gas reclamation system according to claim 9, wherein the generator is configured to supply electric power to a battery.

13. The portable flue gas reclamation system according to claim 12, wherein the battery is provided in an electric vehicle.

14. The portable flue gas reclamation system according to claim 9, wherein the combustion engine is a diesel engine that is configured to operate using waste vegetable oil.

15. The portable flue gas reclamation system according to claim 9, further including at least one set of wheels configured for moving the portable transport apparatus; and
wherein the portable flue gas reclamation system is configured to move from a first location associated with a first building that provides the flue gas to a second location associated with a second building that provides the flue gas using the at least one set of wheels.

16. A method for reclaiming flue gas from a gas source for use in an algae farm, the method comprising:
receiving flue gas from a gas source;
supplying the received flue gas to an intake member of a combustion engine;
providing enriched flue gas from an exhaust outlet of the combustion engine to a compressor;
compressing the enriched flue gas for storage in at least one holding tank; and
supplying the enriched flue gas from the least one holding tank to an algae farm.

17. The method according to claim 16, wherein the combustion engine, the compressor, and the at least one holding tank are disposed inside a portable transport apparatus including at least one set of wheels configured for moving the portable transport apparatus.

18. The method according to claim 17, further comprising:
moving the portable transport apparatus from a first location associated with a first building that provides the received flue gas to a second location associated with a second building that provides the received flue gas using the at least one set of wheels of the portable transport apparatus.

19. The method according to claim 16, further comprising:
using waste heat from the combustion engine for hydrothermal liquefaction of algae in the algae farm.

20. The method according to claim 16, wherein the gas source is a building, and the method further comprising routing the flue gas a first distance from a roof of the building down to the combustion engine located at a ground level near the building.

* * * * *